United States Patent
Filipin

(10) Patent No.: US 12,070,418 B2
(45) Date of Patent: Aug. 27, 2024

(54) MEMBRANE DELAMINATION DEVICE

(71) Applicant: Alcon Inc., Fribourg (CH)

(72) Inventor: Ivan Filipin, Feuerthalen (CH)

(73) Assignee: Alcon Inc., Fribourg (CH)

( * ) Notice: Subject to any disclaimer, the term of this patent is extended or adjusted under 35 U.S.C. 154(b) by 931 days.

(21) Appl. No.: 17/065,693

(22) Filed: Oct. 8, 2020

(65) Prior Publication Data

US 2021/0113377 A1     Apr. 22, 2021

Related U.S. Application Data

(60) Provisional application No. 62/915,705, filed on Oct. 16, 2019.

(51) Int. Cl.
*A61F 9/007*     (2006.01)

(52) U.S. Cl.
CPC ...... *A61F 9/00754* (2013.01); *A61F 9/00709* (2013.01)

(58) Field of Classification Search
CPC .. A61F 9/00754; A61F 9/00709; A61F 9/007; A61F 9/00736; A61F 9/00763; B26B 19/3846; B26B 19/06; B26B 19/20; A61B 17/142; A61B 17/14; A61B 17/320068; A61B 2017/320077

See application file for complete search history.

(56) References Cited

U.S. PATENT DOCUMENTS

| | | | |
|---|---|---|---|
| 9,827,141 B2 | 11/2017 | Schaller | |
| 10,675,180 B2 | 6/2020 | Grueebler | |
| 10,864,001 B2 | 12/2020 | Vezzu | |
| 2008/0319463 A1 | 12/2008 | Hickingbotham | |
| 2015/0238355 A1 | 8/2015 | Vezzu | |
| 2017/0360603 A1* | 12/2017 | Grueebler | ............... A61F 9/007 |
| 2020/0246034 A1 | 8/2020 | Linsi | |
| 2020/0375797 A1 | 12/2020 | Maschio | |
| 2020/0375844 A1 | 12/2020 | Maschio | |

OTHER PUBLICATIONS

Alcon Global Vitreoretinal Product Catalog, dated Feb. 2014, pp. 1 and 25-48.

* cited by examiner

*Primary Examiner* — Ashley L Fishback
*Assistant Examiner* — Chima U Igboko
(74) *Attorney, Agent, or Firm* — Patterson + Sheridan, LLP

(57) ABSTRACT

Particular embodiments disclosed herein provide a membrane delamination device for delaminating a membrane from a retina of an eye. The membrane delamination device comprises an elastic component and a blade element at least partially covered by the elastic component. The blade element comprises a plurality of teeth. The blade element comprises a plurality of blades configured to cut connective tissues between the membrane and the retina. Each of the plurality of blades is positioned between two adjacent teeth of the plurality of teeth.

21 Claims, 5 Drawing Sheets

MEMBRANE DELAMINATION DEVICE

PRIORITY CLAIM

This application claims the benefit of priority of U.S. Provisional Patent Application Ser. No. 62/915,705 titled "MEMBRANE DELAMINATION DEVICE," filed on Oct. 16, 2019, whose inventor is Ivan Filipin, which is hereby incorporated by reference in its entirety as though fully and completely set forth herein.

TECHNICAL FIELD

The present disclosure relates generally to a membrane delamination device for ophthalmic surgery.

BACKGROUND

Membrane removal is a useful surgical treatment for different macular surface diseases. A membrane generally refers to a very thin layer of scar tissue that forms on the surface of the retina. Different types of membranes include epi-retinal membranes (ERM) and proliferative membranes. Each of these membranes may develop as a result of a different eye disease or condition. For example, in the case of ERMs, the scar tissue formation can be associated with a number of ocular conditions, such as prior retinal tears or detachments, or retinal vascular diseases, such as diabetic retinopathy or venous occlusive disease. ERMs can also be developed due to trauma associated with ocular surgery or be associated with intraocular (inside the eye) inflammation. In another example, proliferative membranes may be caused by diabetic retinopathy, which in its advanced form causes new abnormal blood vessels to proliferate (increase in number) on the surface of the retina, thereby forming a proliferative membrane.

Surgical techniques for the removal or peeling of membranes require skill and patience. Precise and carefully constructed surgical instruments are used for each segment of the surgical technique. The surgical treatment itself includes grasping an edge of the membrane, and peeling the membrane. However, peeling certain membranes may pose additional complexities because the membranes may have developed tissues or vessels (referred to herein as "connective tissues") that attach the membranes to the retina. Accordingly, in such cases, the surgeon has to delaminate or remove the connective tissues between the membrane and the retina in order to continue to peel the membrane. Currently, a surgeon may use scissors to delaminate the connective tissue. However, scissors may damage the surface of the retina.

BRIEF SUMMARY

The present disclosure relates generally to a membrane delamination device for ophthalmic surgery.

Particular embodiments disclosed herein provide a membrane delamination device for delaminating a membrane from a retina of an eye. The membrane delamination device comprises an elastic component and a blade element at least partially covered by the elastic component. The blade element comprises a plurality of teeth. The blade element comprises a plurality of blades configured to cut connective tissues between the membrane and the retina. Each of the plurality of blades is positioned between two adjacent teeth of the plurality of teeth.

Particular embodiments disclosed herein provide a handle for delaminating a membrane from a retina of an eye. The handle comprises a hand-grip, a base tip, and a membrane delamination device. The membrane delamination device comprises an elastic component and a blade element at least partially covered by the elastic component. The blade element comprises a plurality of teeth. The blade element comprises a plurality of blades configured to cut connective tissues between the membrane and the retina. Each of the plurality of blades is positioned between two adjacent teeth of the plurality of teeth.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide a membrane delamination device for ophthalmic surgery.

Figure 1:
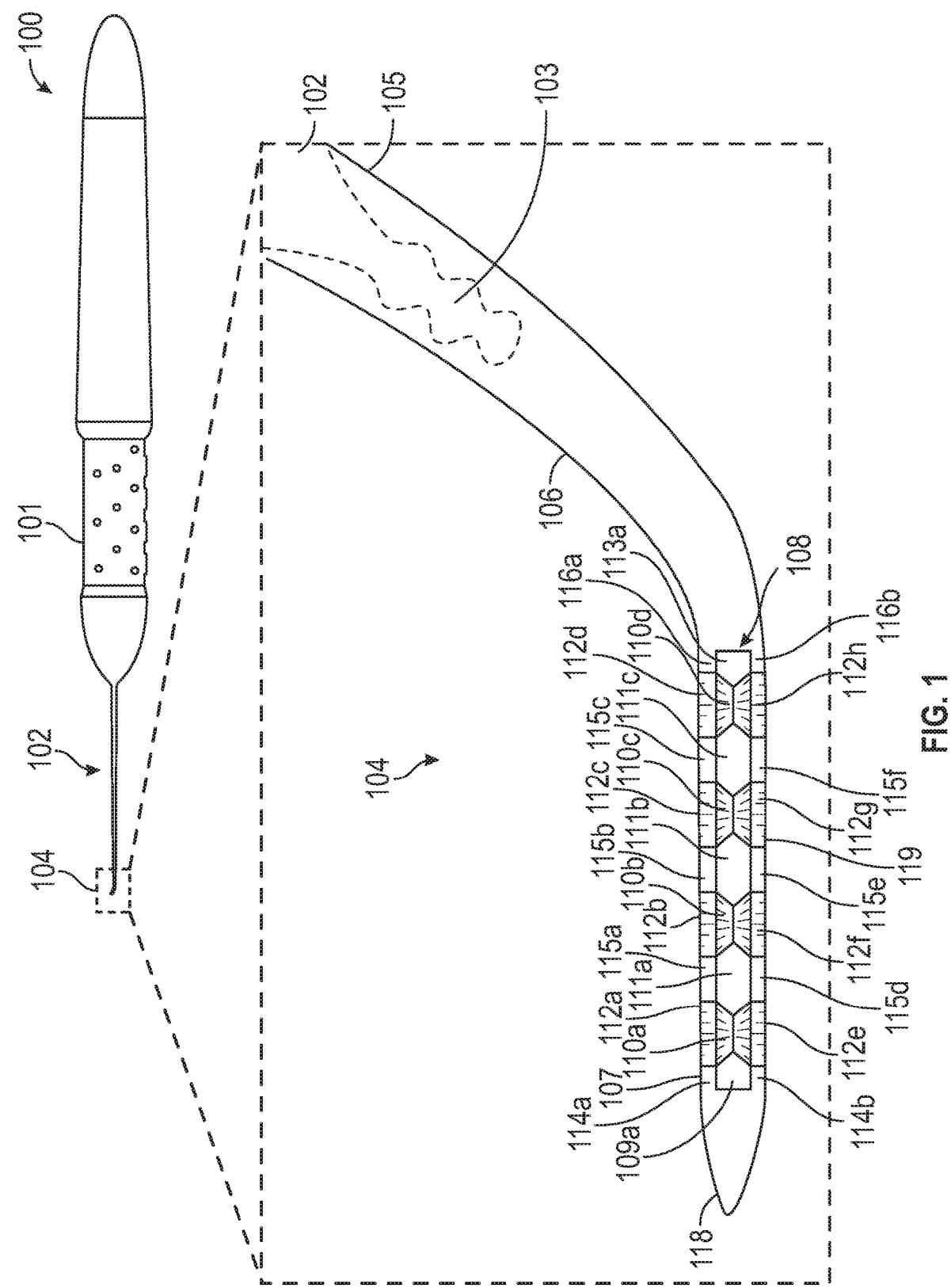
FIG. 1 illustrates an example hand activated handle including a functional tip, in accordance with certain embodiments of the present disclosure.

FIG. 1 illustrates an example hand activated handle 100 (e.g., RENAISSANCE® Handle sold by Alcon Vision, LLC of Fort Worth, TX) including a hand-grip 101, base tip 102, and a functional tip 104. Note that the functional tip 104 is also referred to as a "membrane delamination device." A surgeon may use handle 100 to delaminate a membrane by introducing functional tip 104 of handle 100 to an area between the membrane and the retina. In the example of FIG. 1, functional tip 104 is curved in order to reduce the likelihood of a tip or a distal end 118 of functional tip 104 damaging the surface of the retina. FIG. 1 also shows a more detailed side-view of functional tip 104, which includes an elastic component 106 as well as a blade element 108. Elastic component 106, in certain embodiments, comprises elastic material such as elastic plastic, silicone rubber, or standard plastic (e.g., PC-Makrolon). In certain embodiments, the elastic material that is used may depend on the distance between base tip 102 and blade element 108. For example, if the distance is less than 2 millimeters (mm), silicone rubber may be used. However, if the distance is larger than 2 mm, then standard plastic such as PC-Makrolon may be used.

A proximal end 105 of elastic component 106 is coupled to a distal end 103 of base tip 102. Base tip 102, in certain embodiments, comprises material such as metal. For example, base tip 102 may be a metal wire (e.g., flat wire) made of stainless steel (e.g., stainless steel types 1.4301, 1.4305, or 1.4310). In one example, the proximal end 105 of elastic component 106 and the distal end 103 of base tip 102 may be coupled together using injection molding. In another example, proximal end 105 and distal end 103 may be coupled together using adhesives. As shown, distal end 103 of base tip 102 is shaped such as to create additional static friction between the proximal end 105 and the distal end 103. The higher the static friction between the proximal end 105 and the distal end 103, the lower the likelihood of elastic component 106 separating from base tip 102, and dropping into a patient's eye. In the example of FIG. 1, distal end 103 has a wavy shape that creates more static friction between the proximal end 105 and the distal end 103 as compared to alternative embodiments in which distal end 103 has a straight surface. In other words, the wavy shape of the distal end helps the distal end 103 and proximal end 105 with establishing a strong axial connection together. Also, in the example of FIG. 1, the distal end 103 is a flat wire (e.g., with an oval shape when viewed from the top), which helps the distal end 103 and proximal end 105 with establishing a strong surface connection together, thereby reducing the likelihood of the proximal end 105 rotating around the distal end 103 and becoming loose (as compared to alternative embodiments in which distal end 103 comprises a round wire).

Although not shown, in certain embodiments, distal end 103 of base tip 102 may comprise a male thread (e.g., similar to a bolt) and the proximal end 105 of elastic component 106 may comprise a female thread (e.g., similar to a nut). In such embodiments, the distal end 103 may be screwed into the proximal end 105. Note that, herein, a distal end of a component refers to the end that is closer to a patient's body. On the other hand, the proximal end of the component refers to the end that is facing away from the patient's body.

Figure 2:
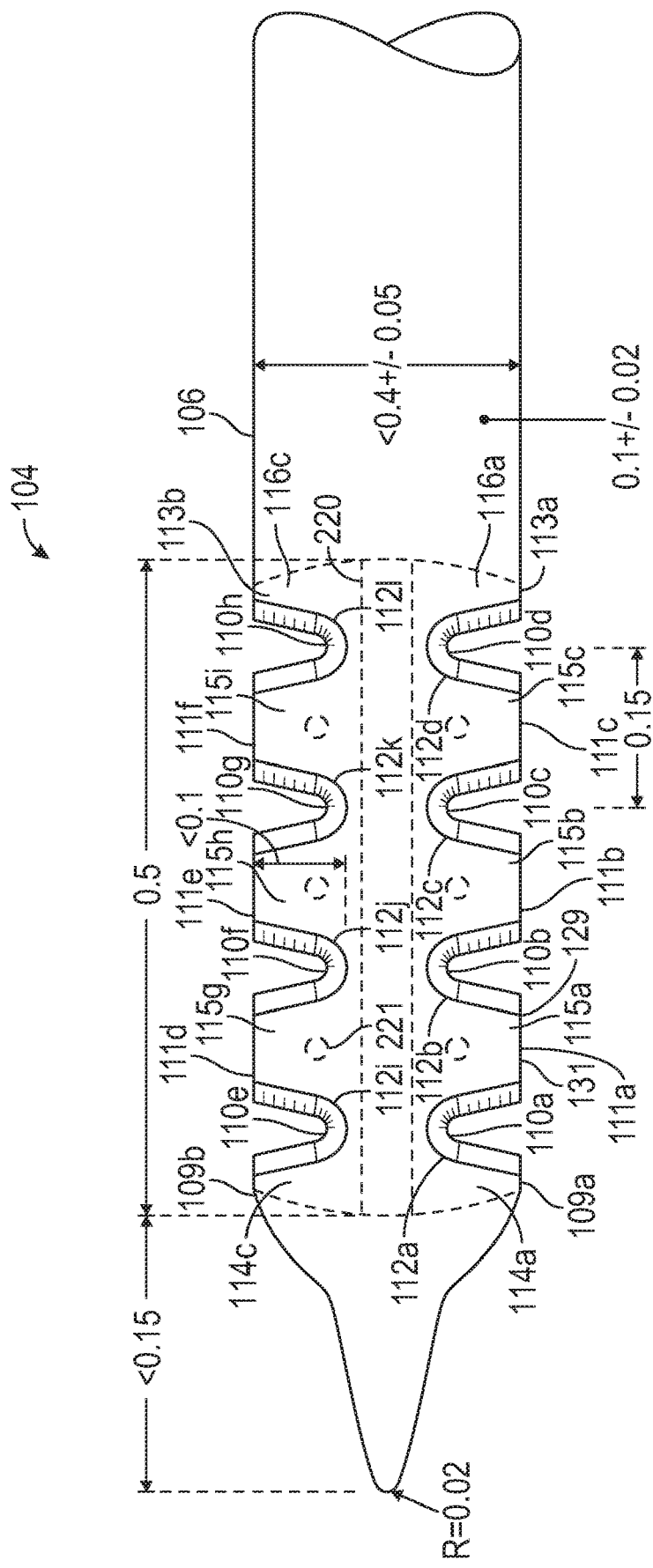
FIG. 2 illustrates an example top view of the functional tip, in accordance with certain embodiments of the present disclosure.

A serrated blade element 108 is embedded within a serrated segment of elastic component 106. Blade element 108 is serrated or toothed such that it comprises a set of teeth on each side for cutting connective tissues between the membrane and the retina. For example, FIG. 1 shows teeth 109a, 111a, 111b, 111c, and 113a on one side of blade element 108. The teeth on the other side of blade element 108 are shown in FIG. 2 as teeth 109b, 111d, 111e, 111f, and 113b. Note that two teeth that are directly next to each other and are on the same side of blade element 108 are referred to herein as being adjacent. However, two teeth that are on the opposite sides of blade element 108 are not referred to as being adjacent even though they may be directly across from each other.

In between teeth 109a, 111a, 111b, 111c, and 113a, blade element 108 comprises sharp edges or blades 110a, 110b, 110c, and 110d. Blade element 108, in certain aspects, comprises metal or similar rigid material. The serrated segment of elastic component 106 comprises a top layer 107 that covers the top surface of blade element 108 and a bottom layer 119 that covers the bottom surface of blade element 108. More specifically, on one side, top layer 107 comprises upper teeth 114a, 115a, 115b, 115c, and 114b that cover teeth 109a, 111a, 111b, 111c, and 113a of blade element 108 from the top while bottom layer 119 comprises lower teeth 114b, 115d, 115e, 115f, and 116b that cover teeth 109a, 111a, 111b, 111c, and 113a from the bottom. In between upper teeth 114a, 115a, 115b, 115c, and 114b of top layer 107 are grooves 112a, 112b, 112c, and 112d while in between lower teeth 114b, 115d, 115e, and 115f, 116b are grooves 112e, 112f, 112g, and 112h.

A surgeon may introduce functional tip 104 from its distal end 118 into an area between a membrane and the retina, such that the bottom layer 119 is placed on or near the surface of the retina and the top layer 107 touches on or near the inner surface of the membrane. As such, in the example herein, top layer 107 is the layer that interfaces with the membrane while bottom layer 119 is the layer that interfaces with the retina. As further shown in FIG. 5, by sliding the functional tip 104 in different directions, connective tissues are severed by the teeth of blade element 108.

Functional tip 104 may be manufactured as a separate component and be coupled to any handle with a base tip, such as base tip 102. For example, functional tip 104 can operate in conjunction with a hand-activated handle, such as handle 100, or an automated handle. An automatic handle may comprise a mechanism for moving functional tip 104 in a manner shown in FIG. 5.

FIG. 2 illustrates an example top view of functional tip 104. More specifically, FIG. 2 illustrates the top layer 107 of elastic component 106 covering blade element 108. Top layer 107 comprises teeth 115a-115c and 115g-115i and a set of grooves 112a-112d and 112i-112l. Blades 110a-110d extend beyond grooves 112a-112d of elastic component 106 on one side while blades 110e-110h extend beyond grooves 112i-112h on the other side. Teeth 109a, 111a-111c, and 113a of blade element 108 are covered from the top by teeth 114a, 115a-115c, and 116a of elastic component 106 while teeth 109b, 111d-111f, and 113b of blade element 108 are covered from the top by teeth 114c, 115g-115i, and 116c of top layer 107. In the embodiments described herein, teeth of blade element 108 and the serrated segment of elastic component 106 have flat tips. For example, the tip 129 of tooth 111a is shown in FIG. 2 as flat. Similarly, tooth 115a of top layer 107 also has a flat tip 131. This is to reduce the likelihood of damage to the retina. In certain other embodiments, the teeth of blade element 108 and the serrated portion of elastic component 106 may have curved tips. As shown, the blades of blade element 108 are semi-circular, U-shaped, or shaped as part an oval, etc. The grooves of the top and bottom layers of the serrated segment of elastic component 106 are also semi-circular, U-shaped, or shaped as part an oval, etc.

As further shown in FIG. 2, blade element 108 also comprises a protruding bar 220 positioned in between teeth 111a-111c and teeth 111d-111f. Protruding bar 220 is shown in FIG. 2 with dashed lines because it is covered by the top layer 107. As further shown in FIG. 3, in certain embodiments, blade element 108 may comprise another protruding bar on its bottom side. Blade element 108 also comprises cylindrical holes 221, shown in dashed lines. In certain embodiments, cylindrical holes 221 are filled or injected with the elastic material of elastic component 106. The elastic material in these cylindrical holes 221 connect the top layer 107 and the bottom layer 119. In certain embodiments, cylindrical holes 221 are perpendicular to the top layer 107 and the bottom layer 119. Cylindrical holes 221 may be filled with elastic material during the injection molding process. Connecting the top layer 107 and the bottom layer 119 helps with holding blade element 108 in place in between the top layer 107 and the bottom layer 119 and, thereby, reducing the likelihood of blade element 108 separating from elastic component 106.

FIG. 2 further illustrates example measurements of the different portions of functional tip 104. For example, the width of elastic component 106 at its widest segments may be about 0.4+/−0.05 mm. Also, the thickness of elastic component 106, at its non-serrated segment, may be about 0.1+/−0.02 mm. The length of blade element may be about 0.5 mm while the distance between the mid points of any two adjacent blades, such as blades 110c and 110d, may be about 0.15 mm. Each one of teeth 109a-109b, 111a-111f, and 113a-113b may have a width of about 0.1 mm measured from its base. For example, tooth 111e may have a width of 0.1 mm. The distal end 118 of functional tip 104 may have a length of about 0.15 mm measured from a distal end of blade element 108. The distal end 118 of functional tip 104 may include a pointed tip with a radius of about 0.02 mm (other radii are also possible). The distal end 118 is configured with the pointed tip to allow a surgeon to more easily introduce or guide functional tip 104 into the area between the membrane and the retina. The pointed tip may be curved so as to not damage the surface of the retina, should there be any contact between the two. Other measurements for the function tip 104 that are appropriate for retina surgery are also contemplated.

Note that although blade element 108 comprises five teeth on each of its sides, in certain other embodiments a blade element may comprise a larger or a smaller number of teeth on each of its sides. Also, in another embodiments, a blade element may have teeth on only one of its sides.

Figure 3:
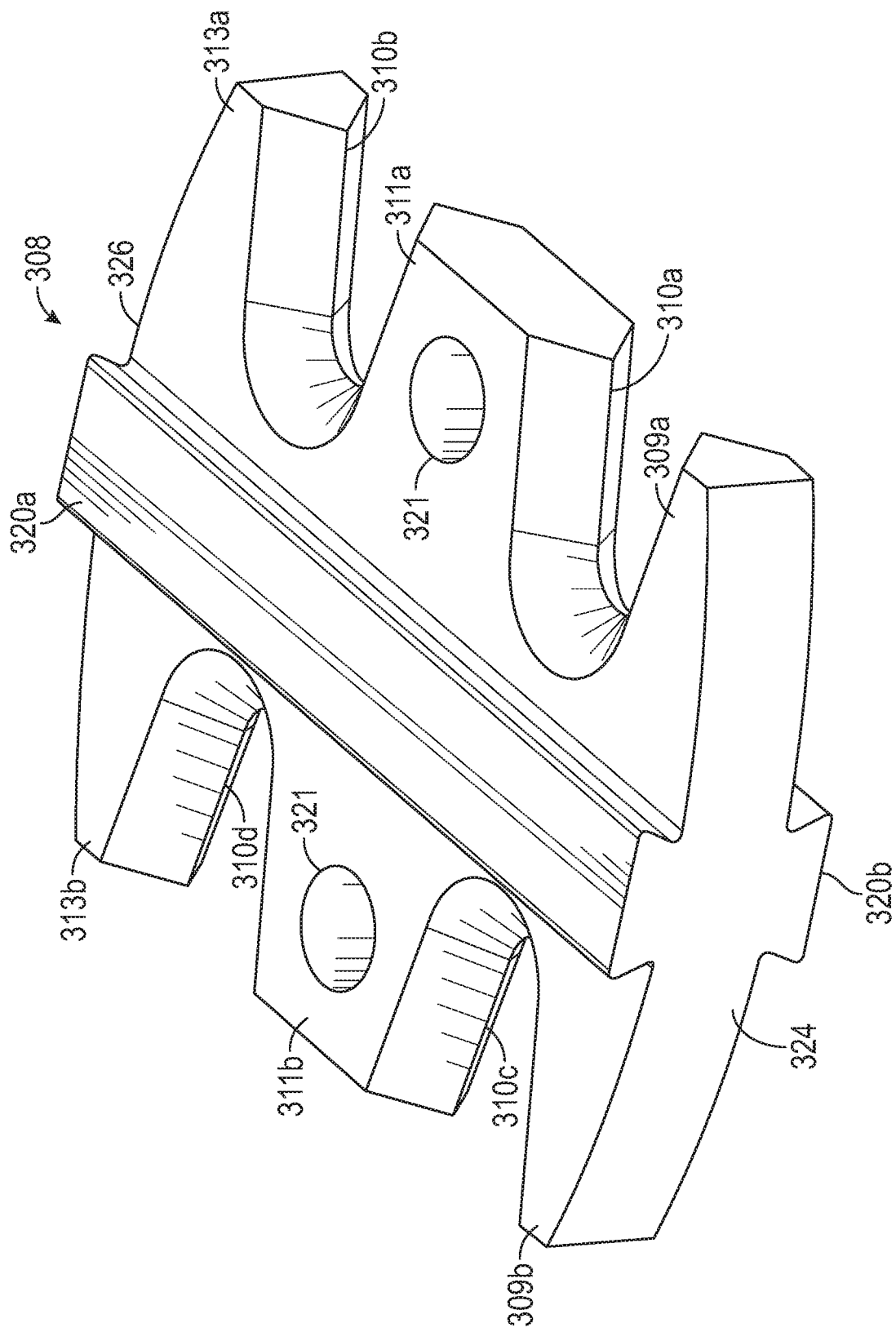
FIG. 3 illustrates an example blade element with teeth blades on both sides, in accordance with certain embodiments of the present disclosure.

FIG. 3 illustrates an example blade element 308 with teeth 309a, 311a, and 313a on one side and 309b, 311b, and 313b on the other side. In-between teeth 309a, 311a, and 313a, blade element 308 includes blades 310a and 310b while in-between teeth 309b, 311b, and 313b, blade element 308 includes blades 310c and 310d. As shown, blades 310a-310d include sharp edges for cutting connective tissues between a membrane and the retina. Blade element 308 is different from blade element 108 in that blade element 308 is shorter and comprises a smaller number of teeth and blades. As shown, blade element 308 comprises a protruding bar 320a on top and another protruding bar 320b on the bottom. Blade element 308 further comprises two ends, including end 324 and end 326, which may both curved.

Figure 4:
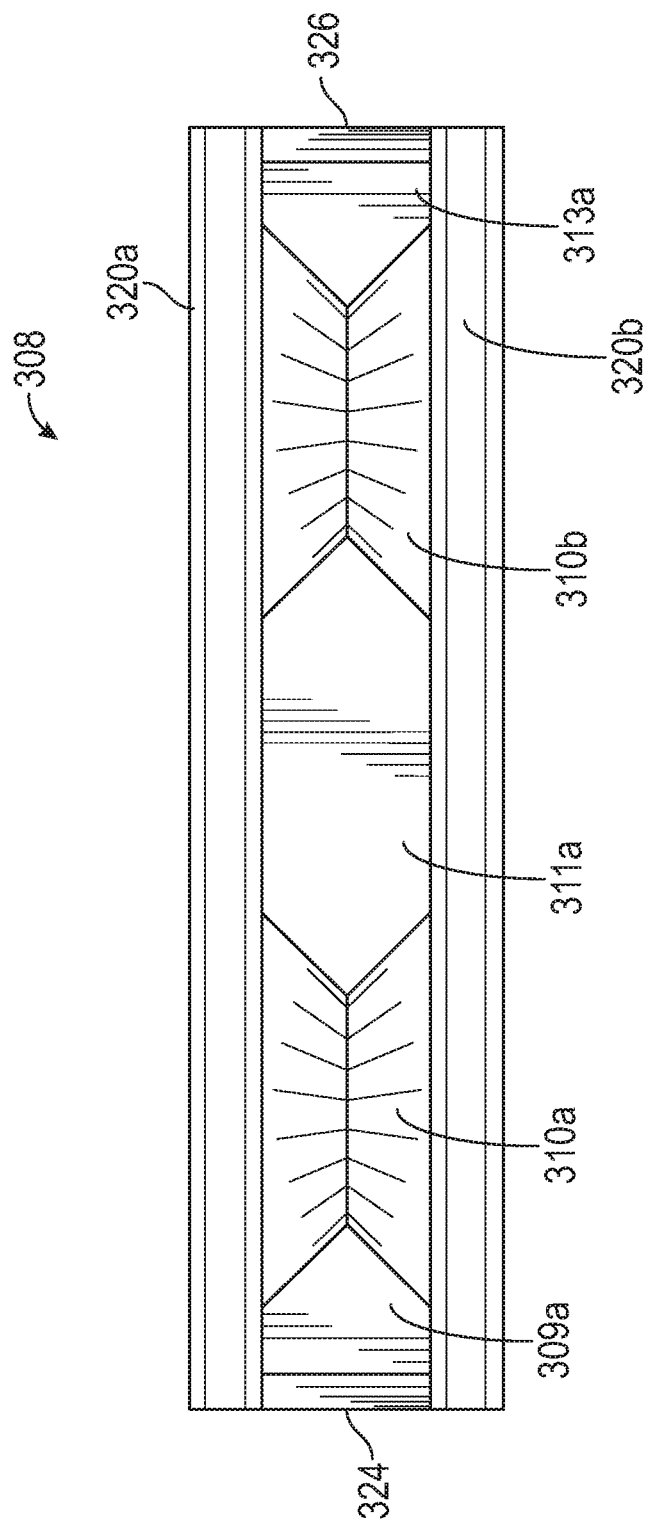
FIG. 4 illustrates a side view of the blade element of FIG. 3, in accordance with certain embodiments of the present disclosure.

FIG. 4 illustrates a side view of the blade element 308 of FIG. 3. As shown, blade element 308 includes teeth 309a, 311a, and 313a and, in-between those teeth, blade element 308 comprises blades 310a and 310b. Blade element 308 also comprises protruding bars 320a and 320b. FIG. 4 also illustrates the curved ends 324 and 326 of blade element 308.

Figure 5:
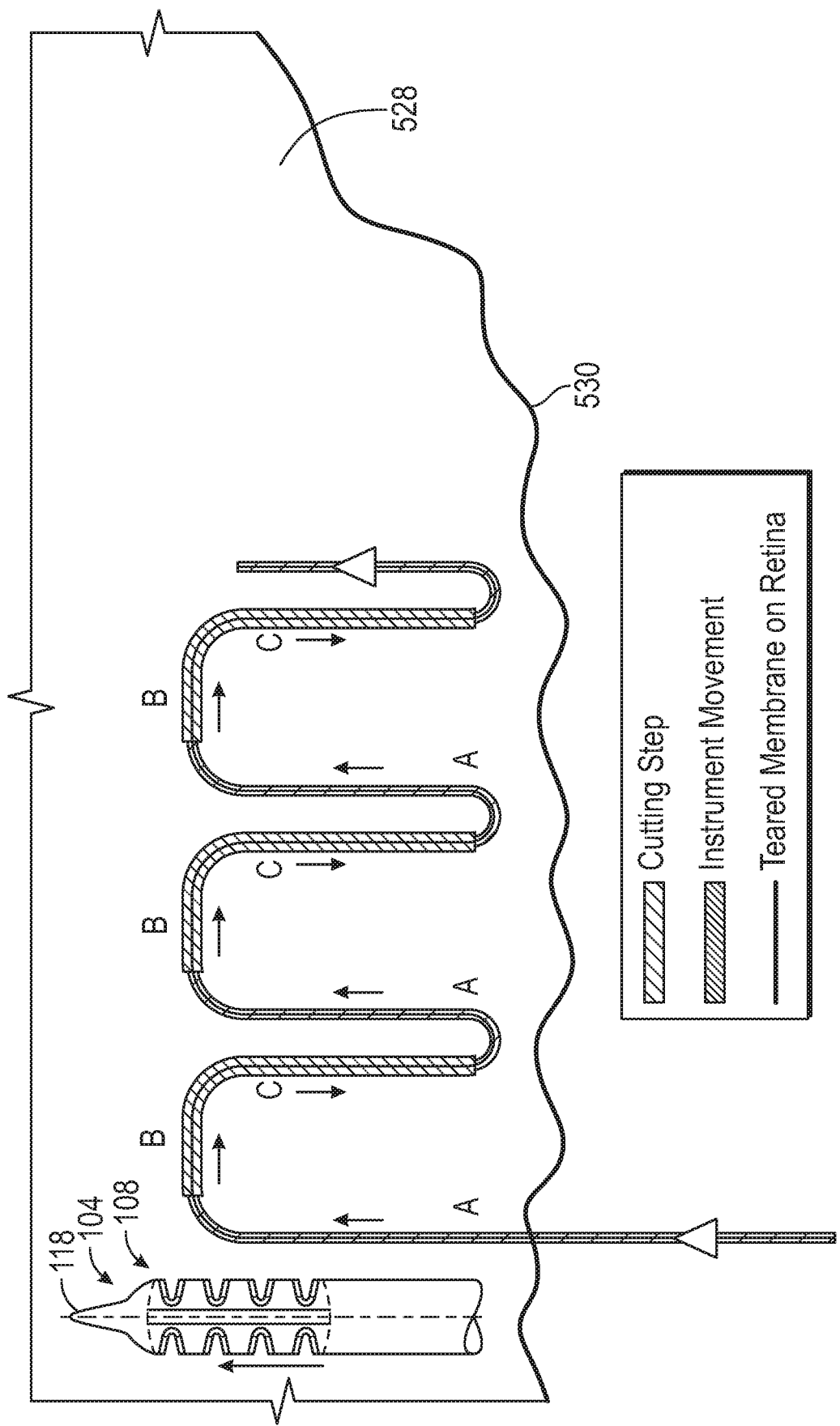
FIG. 5 illustrates an example path of movement of the functional tip for cutting connective tissues between a membrane and the retina, in accordance with certain embodiments of the present disclosure.

FIG. 5 illustrates an example path of movement of functional tip 104 for cutting connective tissues between a membrane 528 and the retina. For example, a surgeon may grasp an edge 530 of membrane 528 and then use a handle, such as handle 100 of FIG. 1, to introduce the functional tip 104 into an area between membrane 528 and the retina by using the distal end 118 of functional tip 104 as a guide. After inserting the functional tip 104 deep enough (e.g., step A), the surgeon may move functional tip 104 sideways (e.g., step B) and then pull functional tip 104 towards the edge 530 of membrane 528 (e.g., step C). As shown, the cutting of the connective tissues occurs when the surgeon moves functional tip 104 sideways (e.g., to the right, in the example of FIG. 5) and towards the edge 530 of membrane 528. The surgeon may continue to repeat these three movements or steps until all connective tissues between membrane 528 and the retina are removed, after which the surgeon is able to peel off the membrane.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A membrane delamination device for delaminating a membrane from a retina of an eye, comprising:
   an elastic component;
   a blade element coupled to the elastic component, wherein:
     the blade element comprises a plurality of teeth;
     the blade element comprises a plurality of blades configured to cut connective tissues between the membrane and the retina; and
     each of the plurality of blades is disposed within a groove formed in the elastic component and positioned between two adjacent teeth of the plurality of teeth.

2. The membrane delamination device of claim 1, wherein the elastic component is configured to be coupled to a base tip of a handle.

3. The membrane delamination device of claim 2, wherein a proximal end of the elastic component is coupled to a distal end of the base tip using injection molding.

4. The membrane delamination device of claim 1, wherein:
   the elastic component comprises a distal end that is pointed; and
   the pointed distal end acts as a guide for inserting the membrane delamination device into an area between the membrane and the retina.

5. The membrane delamination device of claim 1, wherein the elastic component comprises plastic.

6. The membrane delamination device of claim 1, wherein:
   the plurality of teeth comprise a first plurality of teeth positioned on a first side of the blade element and a second plurality of teeth positioned on a second side of the blade element; and
   the plurality of blades comprise a first plurality of blades associated with the first plurality of teeth and a second plurality of blades associated with the second plurality of teeth.

7. The membrane delamination device of claim 6, wherein:
   the elastic component comprises a serrated segment comprising a first layer and a second layer;
   the first layer comprises a third plurality of teeth for covering the first plurality of teeth and the second plurality of teeth from a third side of the blade element; and
   the second layer comprises a fourth plurality of teeth for covering the first plurality of teeth and the second plurality of teeth from a fourth side of the blade element.

8. The membrane delamination device of claim 7, wherein the first layer interfaces with the membrane and the second layer interfaces with the retina.

9. The membrane delamination device of claim 7, wherein:

the blade element comprises cylindrical holes perpendicular to the first layer and the second layer; and the first layer and the second layer are connected to hold the blade element in place through material injected in the cylindrical holes that connect the first layer and the second layer.

10. The membrane delamination device of claim 7, wherein the blade element comprises a first protruding bar on the third side and a second protruding bar on the fourth side.

11. The membrane delamination device of claim 1, wherein each of the plurality of blades is at least one of semi-circular, U-shaped, or shaped as part of an oval.

12. A handle for delaminating a membrane from a retina of an eye, comprising: hand-grip;
a base tip;
a membrane delamination device, comprising:
an elastic component configured to be coupled to the base tip;
a blade element at least partially covered by the elastic component, wherein:
the blade element comprises a plurality of teeth;
the blade element comprises a plurality of blades configured to cut connective tissues between the membrane and the retina; and
each of the plurality of blades is disposed within a groove formed in the elastic component and positioned between two adjacent teeth of the plurality of teeth.

13. The handle of claim 12, wherein the elastic component is configured to be coupled to the base tip of a handle.

14. The handle of claim 12, wherein a proximal end of the elastic component is coupled to a distal end of the base tip using injection molding.

15. The handle of claim 12, wherein:
the elastic component comprises a distal end that is pointed; and
the pointed distal end acts as a guide for inserting the membrane delamination device into an area between the membrane and the retina.

16. The handle of claim 12, wherein the elastic component comprises plastic.

17. The handle of claim 12, wherein:
the plurality of teeth comprise a first plurality of teeth positioned on a first side of the blade element and a second plurality of teeth positioned on a second side of the blade element; and
the plurality of blades comprise a first plurality of blades associated with the first plurality of teeth and a second plurality of teeth associated with the second plurality of teeth.

18. The handle of claim 17, wherein:
the elastic component comprises a serrated segment comprising a first layer and a second layer;
the first layer comprises a third plurality of teeth for covering the first plurality of teeth and the second plurality of teeth from a third side of the blade element; and
the second layer comprises a fourth plurality of teeth for covering the first plurality of teeth and the second plurality of teeth from a fourth side of the blade element.

19. The handle of claim 18, wherein the first layer interfaces with the membrane and the second layer interfaces with the retina.

20. The handle of claim 18, wherein:
the blade element comprises cylindrical holes perpendicular to the first layer and the second layer; and
the first layer and the second layer are connected to hold the blade element in place through material injected in the cylindrical holes that connect the first layer and the second layer.

21. The handle of claim 18, wherein the blade element comprises a first protruding bar on the third side and a second protruding bar on the fourth side.

* * * * *